US006198287B1

(12) United States Patent
Heiserholt et al.

(10) Patent No.: US 6,198,287 B1
(45) Date of Patent: Mar. 6, 2001

(54) ELECTRICAL APPARATUS HAVING COMPONENTS DISPOSED INSIDE AND OUTSIDE OF A HIGH-FREQUENCY SHIELDED ROOM

(75) Inventors: Georg Heiserholt; Michael Kramer, both of Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/086,279

(22) Filed: May 28, 1998

(30) Foreign Application Priority Data

May 28, 1997 (DE) .............................................. 197 22 221

(51) Int. Cl.[7] ...................................................... G01U 3/00
(52) U.S. Cl. ............................................ 324/322; 324/318
(58) Field of Search ..................................... 324/318, 322, 324/307, 309, 314

(56) References Cited

U.S. PATENT DOCUMENTS

| 4,737,712 | * | 4/1988 | Stormont et al. ..................... 324/307 |
| 4,763,075 | * | 8/1988 | Weigert ................................. 324/318 |
| 5,545,999 | * | 8/1996 | Mueller et al. ....................... 324/322 |

* cited by examiner

*Primary Examiner*—Louis Arana
(74) *Attorney, Agent, or Firm*—Hill & Simpson

(57) ABSTRACT

A diagnostic magnetic resonance apparatus has at least one component arranged inside a high-frequency shielded room, at least one other component arranged outside the high-frequency shielded room, and a control computer which is connected with the components via control lines. The control lines are constructed as a serial sensor/actuator bus comprising a first bus portion with electrical bus lines, and a second bus portion with optical bus lines. The optical bus lines are conducted into the high-frequency shielded room and are connected therein with the first component. The first bus portion is connected with the second bus portion via an electro-optical interface.

11 Claims, 4 Drawing Sheets

ELECTRICAL APPARATUS HAVING COMPONENTS DISPOSED INSIDE AND OUTSIDE OF A HIGH-FREQUENCY SHIELDED ROOM

BACKGROUND OF THE INVENTION

1. Field of the Invention

The present invention relates to an electrical apparatus of the type having at least one first component arranged within a high-frequency shielded room (or chamber or cubicle), and at least one second component arranged outside the high-frequency shielded room, and having a control computer which is connected to the components via control lines.

2. Description of the Prior Art

An electrical apparatus of the above type in the form of a diagnostic magnetic resonance device is described in overview in the book "Bildgebene Systems for die Medizinische Diagnostik," (Heinz Morneburg. pub.; 3, edition, 1995, Publicis MCD Veriag: pp 501–503). Roughly divided, the magnetic resonance device includes components which are arranged inside a high-frequency shielded room and components which are arranged outside the high-frequency shielded room. The diagnostic magnetic resonance device is controlled by a control computer arranged outside the high-frequency screening cabin. Control of the components arranged outside the screening cabin therein ensues via a central bus. To avoid disturbances in the operation of the magnetic resonance device, the components arranged inside the high-frequency shielded room are either powered with control signals via light waveguides or are turned off during a measuring sequence. Heretofore, the light radially from the control computer to the individual components in the high-frequency shielded room. This placement is costly and complex. In addition, besides being loaded by making the individual control signals, available the control computer is loaded by the communication with the individual components.

Known techniques in the data processing field for relieving a control computer of communications tasks, which employ extra or subsidiary electrical data exchange lines, cannot be used here, since any feeding of electrical data lines into the high-frequency shielded room would disturb the highly sensitive magnetic resonance measurement. Filtering and shielding of such a data bus would be costly and would severely limit the data transmission rate.

German OS 196 25 997 discloses CAN bus (Controller Area Network bus) for driving elements of a machine with at least one bus coupling element, to which a device can be connected by means of an optical transmission path. The data transmission with the optical transmission path assures a simple, reliable, and rapid adjustment or shifting of the respective elements of the machine. Instead of peripheral devices connected to the CAN bus, nodes can be provided—preferably stellar nodes—from which a number of light guides in turn lead to other stellar nodes and/or peripheral devices.

German OS 196 16 753 discloses a device and a method for controlling a data transmission channel or data bus over which data are transmitted according to a prescribe transmission protocol or bus protocol in a bit-serial fashion, e.g. a CAN bus.

Shielded rooms for high-frequency magnetic fields, particularly for NMR tomography systems in medical technology, are described in German PS 38 09 323, and German Utility Model G 90 17 344.9, for example.

SUMMARY OF THE INVENTION

It is an object of the present invention to provide an electrical apparatus having a shielded room and a control computer disposed outside of the shielded room which communicates with at least one component inside the shielded room and with at least one other component outside the shielded room, wherein the control computer is relieved of communications tasks without simultaneously creating disturbances inside the high-frequency shielded room.

The object is achieved in an electrical apparatus wherein the control lines are constructed as a serial sensor/actuator bus, the sensor/actuator bus having a first bus portion with electrical bus lines and a second bus portion with optical bus lines, with the optical bus lines being conducted into the high-frequency cabin and connected with a component therein, and wherein the first bus portion is connected to the second bus portion via an electro-optical interface.

A common bus can then be used to control the components; the control computer is relieved of communications tasks. The advantages of the electrical bus portion—which has a low outlay associated therewith—are available in the uncritical space outside the high-frequency shielded room, while the abovementioned compatibility problems in the high-frequency shielded room are simultaneously avoided by the use of light guides. The electrical portion of the bus is transferred into the optical portion via the electro-optical interface, and vice versa.

In an embodiment the sensor/actuator bus is constructed as a Controller Area Network bus (CAN bus). The CAN bus is constructed simply and is insensitive to disturbance. In addition, structural elements which meet the CAN bus specifications are available from several manufacturers.

DESCRIPTION OF THE PREFERRED EMBODIMENTS

Figure 1:
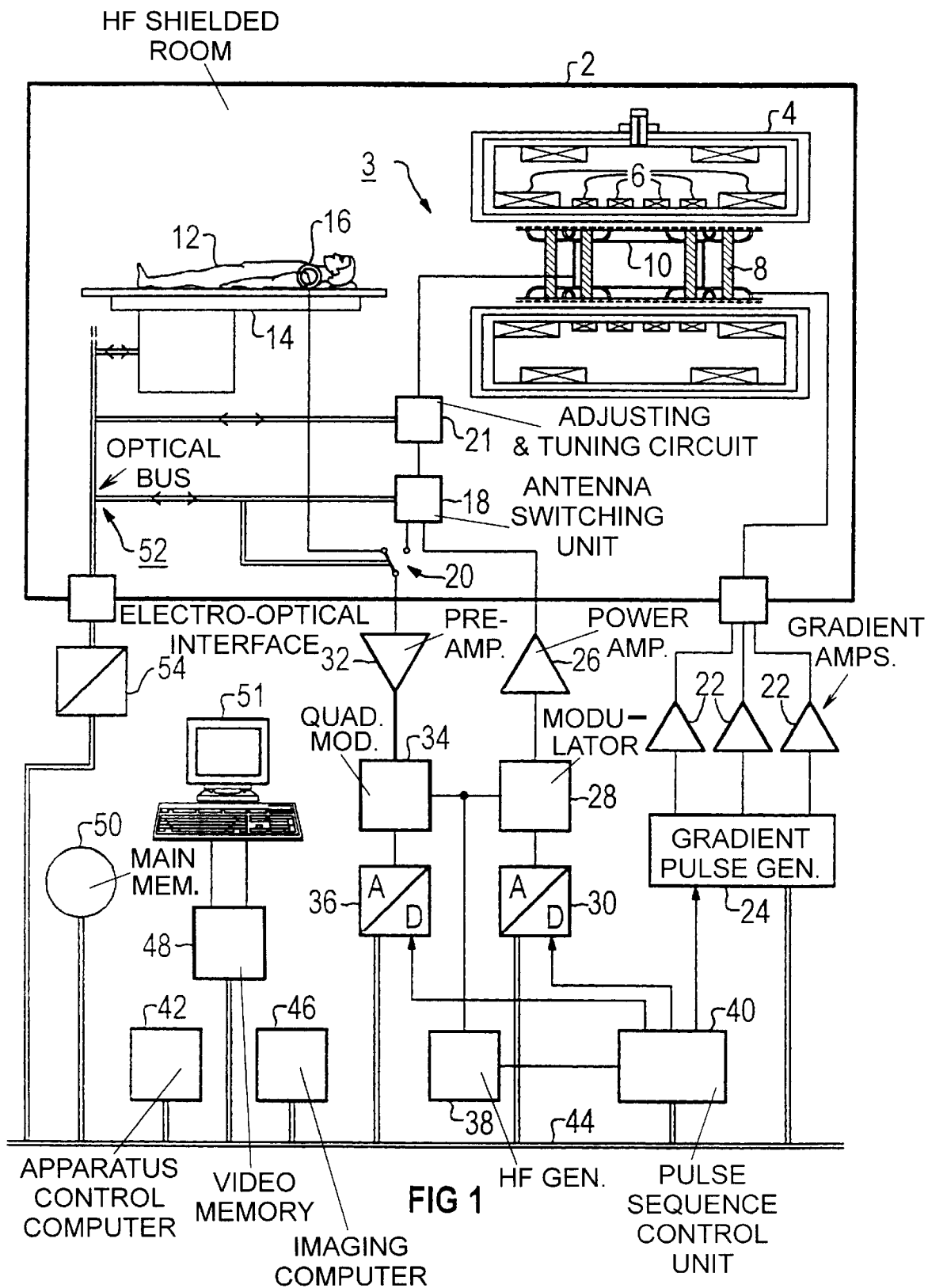
FIG. 1 is a block diagram showing the basic components of a diagnostic magnetic resonance apparatus constructed in accordance with the invention.

Although the basic construction of a diagnostic magnetic resonance device is well-known, the principal components of a device are first outlined herein. The actual examination instrument of the diagnostic magnetic resonance device is located inside a high-frequency shielded room 2. As the largest structural unit, it contains a magnet 3 for creating a homogenous static magnetic field. Inside an annular housing 4, there are superconductive field coils 6 which create—in the cylindrical interior—a main magnetic field oriented in the axial direction of the magnet 3. In the interior of the magnet (warm bore), a gradient coil set 8 is incorporated, to which a whole-body high-frequency antenna 10 is connected in the interior, this being constructed for accepting a patient 12. A movable patient bed 14 is provided for orienting and transporting the patient 12 into the interior. Local antennas 16 for examining specific body regions can be used.

An antenna switching unit 18 and a change-over switch 20 are arranged inside the shielded room 2 for operating the high-frequency antenna 10, the local antenna 16 or an array of antennas. The high-frequency antenna 10 can be tuned and adjusted to the line resistance by means of an adjusting and tuning circuit 21. Outside the high-frequency shielded room 2, there are components for driving the gradient coil set 8, which include a gradient coil amplifier 22 and a gradient pulse generator 24. Also arranged outside the shielded room 2 are the high-frequency components for transmitting and receiving the high-frequency magnetic resonance signals. This includes a power amplifier 26, a modulator 28 and a digital-analog converter 30 in the transmitting channel. The high-frequency reception channel includes a preamplifier 32, a quadrature modulator 34 and an analog-digital converter 36. The modulator 28 and the demodulator 34 are connected to a high-frequency generator 38. The digital-analog converter 30, the analog-digital converter 36 and the gradient pulse generator 24 are powered with control signals from a pulse sequence control nuit 40. An apparatus control computer 42 controls the components arranged outside the high-frequency shielded room 2—e.g. the gradient pulse generator 24, the digital-analog converter 30, the analog-digital converter 36, and the pulse sequence control unit 40—via a central bus 44. In addition, an imaging computer 46, a video memory 48 and a main memory 50 are connected to the central bus 44. For operating and controlling the magnetic resonance device, an operating desk with monitor 51 is connected with the central bus 44 via the video memory 48.

While the central bus 44 outside the high-frequency shielded room 2 is realized as electrical bus portion with electrical bus lines, the components arranged inside the high-frequency cabin—e.g. the patient bed 14, the antenna switching unit 18, the change-over switch 20 and the adjusting and tuning circuit 21 are connected to optical bus lines via a second bus portion 52. The electrical bus portion 44 and the optical bus portion 52 are mutually coupled via an electro-optical interface 54, so that the two bus portions form a unified sensor-actuator bus.

Figure 2:
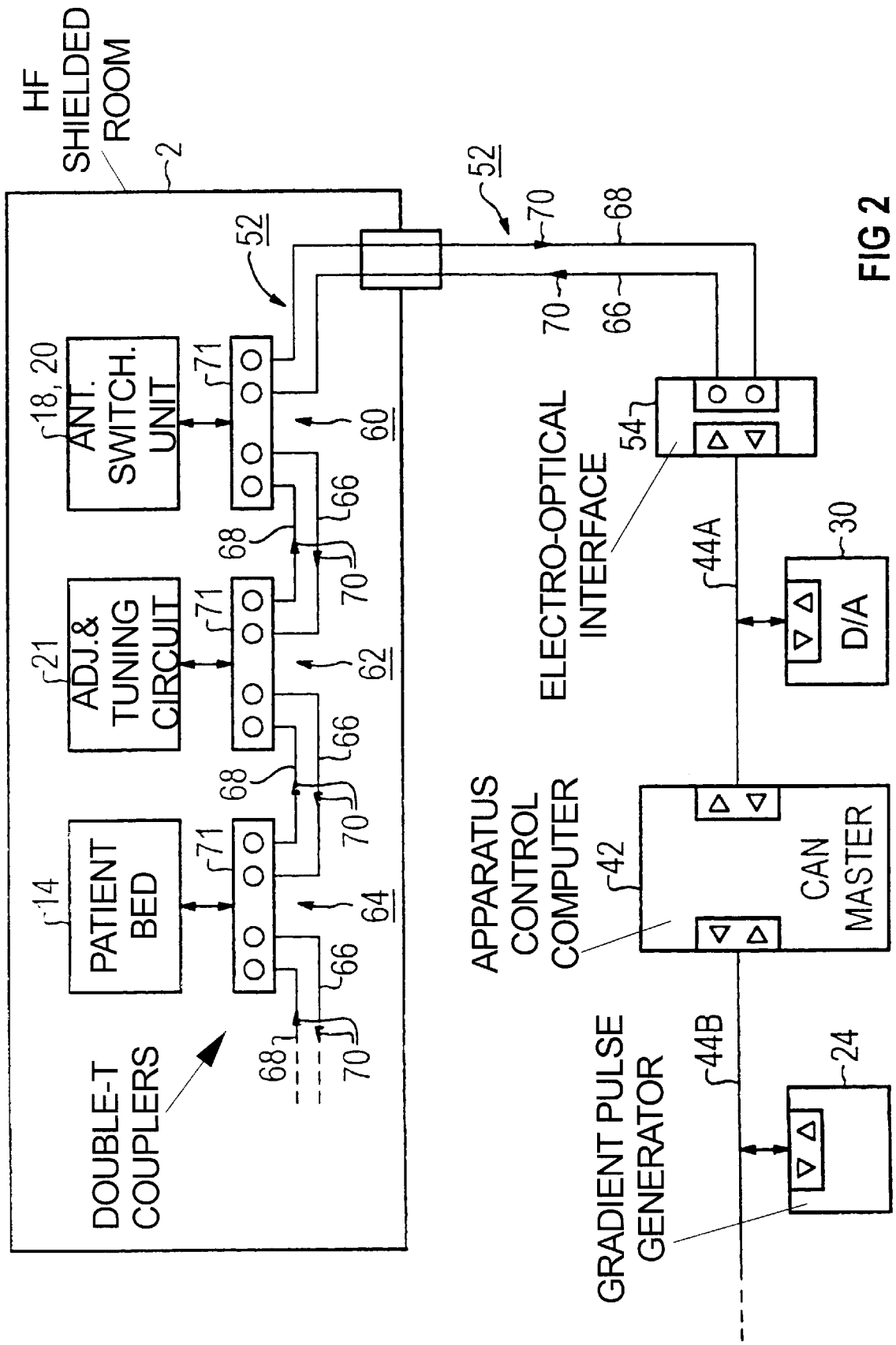
FIG. 2 is a block diagram showing an electro-optical mixed bus, for use in the inventive diagnostic magnetic resonance apparatus of FIG. 1.

In a block diagram, FIG. 2 shows the bus structure utilized to control the magnetic resonance device. The bus is realized as a Controller Area Network bus (CAN bus). The components connected to the bus represent nodes which monitor the data on the bus and—if an acceptance test on the identifier connected to a data packet is positive—take this data over or bring data onto the bus themselves. Although the CAN bus basically permits a multi-master bus operation, the components connected thereto are controlled therein essentially through the apparatus control computer 42 only. As the first node, the apparatus control computer 42 is therein designated as CAN MASTER. From the apparatus control computer 42, a right electrical bus portion 44A and a left electrical bus portion 44B originate. The right electrical bus portion 44A is first connected to a second node— which brings about the data exchange with the transmitter 30—and then to the electro-optical interface 54. The electro-optical interface 54 transfers the electrical CAN bus into the optical bus that satisfies the CAN specifications. The bit level typically prevailing for the CAN bus is realized by "light on" and the typically recessive bit level is realized by "light off". This optical bus portion 52 is led in sequence to the individual components inside the shielded room 2. As the first node 60 in the optical bus portion 52, the antenna switching unit 18 and the change-over switch 20 are connected to the bus. Via a second node 62, the adjusting and tuning unit 21 for the whole-body antenna 10 is connected to the bus. Via a third node 64, the patient bed 14 is connected to the bus. The optical bus portion 52 can be expanded via the node 64. At the left part of the electrical bus portion 44B, at another node, the gradient pulse generator 24 and further external components are connected. The electrical bus portion 44B can be expanded as needed.

The electrical bus portion 44 (including portions 44A and 44B) is constructed in known fashion as a stranded two-wire (twisted pair) circuit. The optical bus portion 52 utilizes a double light waveguide. Proceeding from the electro-optical interface 54 up to the first node 60 and then in sequence to the other nodes 62, 64, etc., two light guide segments 66, 68 are respectively used. The data flow on the light guide segments 66, 68 is designated by arrows 70. The arrows 70 respectively point from an optical transmitter to an optical receiver, which are arranged in optical double-T couplers 71. A double-T coupler 71 is allocated to each node 60, 62, 64 in the optical bus portion 52.

Figure 3:
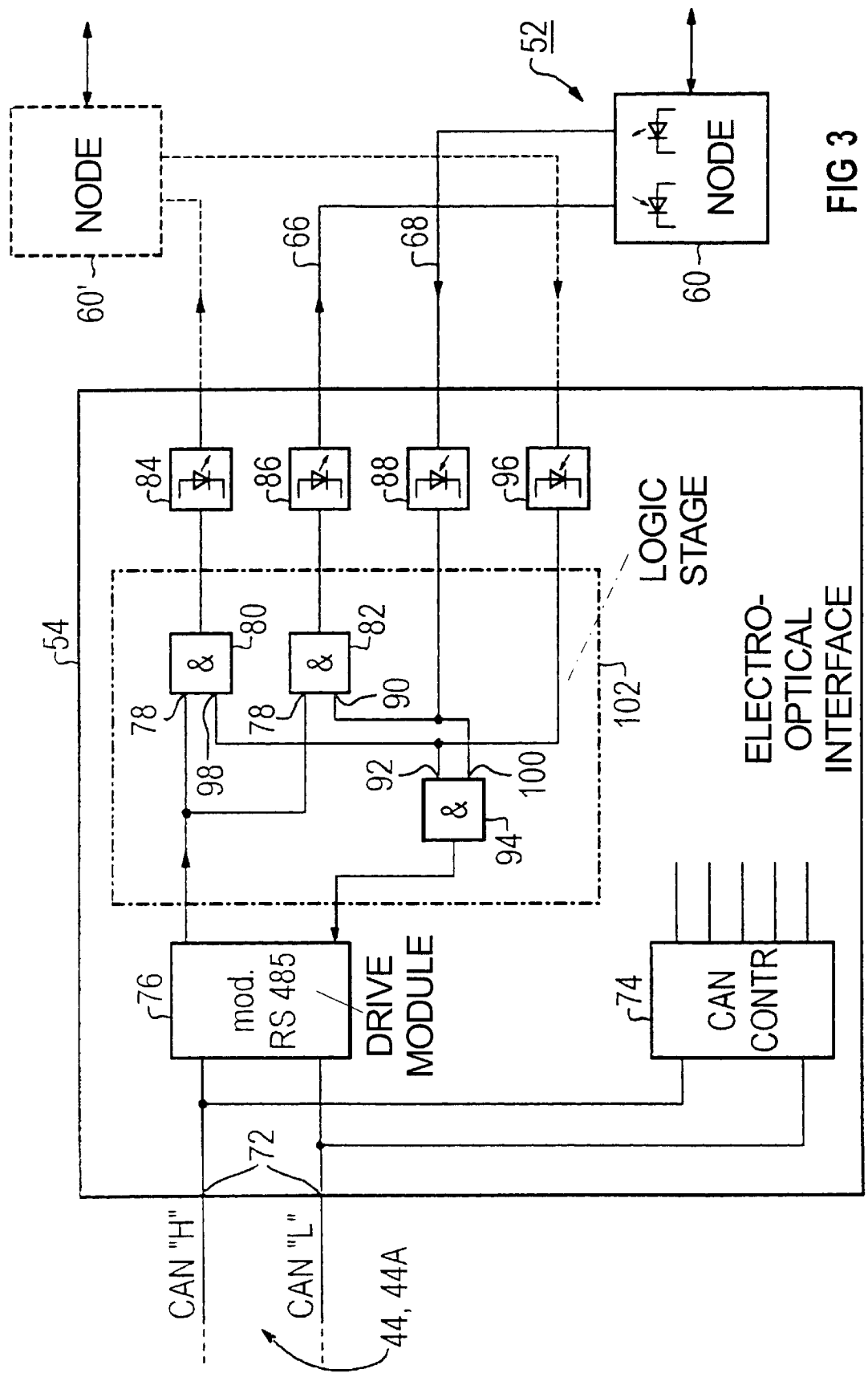
FIG. 3 is a block diagram showing an electro-optical interface, for use in the inventive diagnostic magnetic resonance apparatus of FIG. 1.

In a block diagram, FIG. 3 depicts the construction of the electro-optical interface 54, which transfers the electrical bus portion 44 in the optical bus portion 52, and vice versa. The interface 54 is constructed, such that it can be inserted in an optical bus portion. If the electro-optical interface is inserted in the optical bus, two neighboring nodes 60 and 60' can be connected.

The electro-optical interface 54 has a terminal 72 for the electrical bus portion 44, or 44A. The terminal 72 is connected with a CAN controller module 74—e.g. in the form of a 57C360 module—and with a modified RS-485 drive module 76. An output of the RS-485 drive module 76 is connected with an input 78 of an AND gate 80 and an AND gate 82. The output of the AND gate 80 is connected with a first optical transmitter 84, and the output of the AND gate 82 is connected with a second optical transmitter 86. A first optical receiver 88 is connected with a second input 90 of the AND gate 82 and with a first input 92 of another AND gate 94. The electrical output of another optical receiver 96 is connected with a second input 98 of the AND gate 80 and with a second input 100 of the AND gate 94. The output of the AND gate 94 is connected with an input of the modified RS-485 drive 76. The three AND gates 80, 82 and 94 together form a logic stage 102, with which a signal exchange is possible with the node 60 and with a further node 60', which may be connected . Furthermore, the logic stage 102, along with the modified RS-485 drive 76, effects a signal exchange with the electrical bus portion 44, 44A and with the optical bus portion 52, this being supported by the CAN controller 74.

Figure 4:
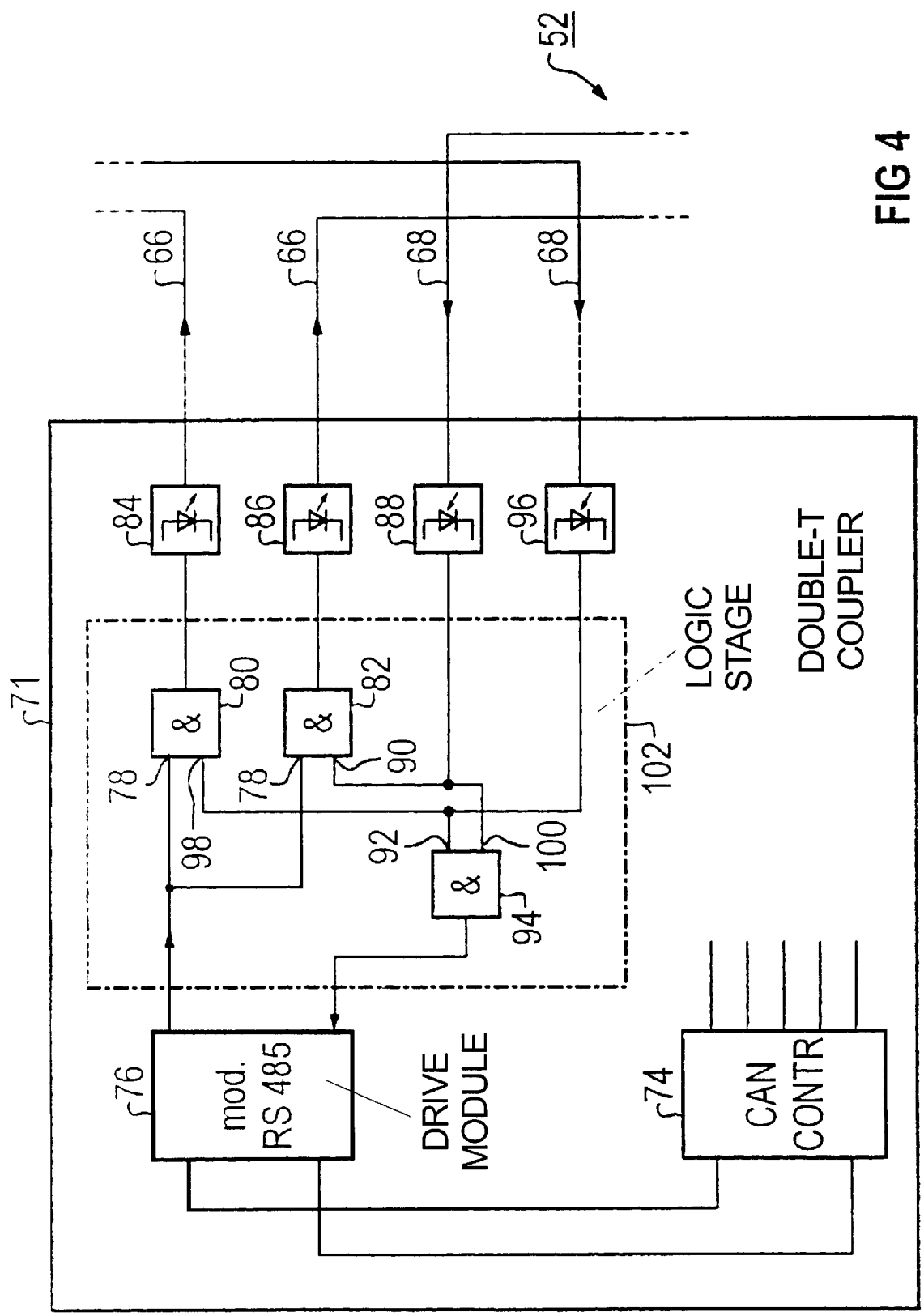
FIG. 4 is a block diagram showing an optical double-T piece for use in the inventive diagnostic magnetic resonance apparatus of FIG. 1.

FIG. 4 depicts the structure of an optical double-T coupler 71, which corresponds to the structure of the electro-optical interface 54—up to the electrical bus terminal 72. The optical double-T coupler 71 permits a data exchange with neighboring nodes, wherein a repeater function is additionally performed. If, for example, the double-T coupler 71 is allocated to the node 62, then a data exchange with the nodes 60 and 64 can be performed via the two neighboring double-T couplers. The double-T coupler 71 allocated to the node 60 performs a data exchange—with repeater function—with the neighboring double-T coupler 71 of the node 62 and with the electro-optical interface 54.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electrical apparatus comprising:

a high-frequency shielded volume;

a first component disposed inside said high-frequency shielded volume;

a second component disposed outside of said high-frequency shielded volume;

a control computer connected to said first component and to said second component via control lines comprising a serial sensor/actuator bus; and said sensor/actuator bus comprising a first bus portion formed exclusively by electrical bus lines and a second bus portion formed exclusively by optical bus lines, said optical bus lines being conducted into said high-frequency shielded volume and being connected therein to said first component, and said first bus portion being disposed outside of said high-frequency shielded volume and being connected to said second bus portion via an electro-optical interface.

2. An electrical apparatus as claimed in claim 1 further comprising a plurality of additional components disposed in said high-frequency shielded volume, and further comprising a plurality of optical double-T couplers respectively connecting said first component and said plurality of additional components to said optical bus lines.

3. An electrical apparatus as claimed in claim 2 wherein said plurality of optical double-T couplers each have a repeater function.

4. An electrical apparatus as claimed in claim 2 wherein said second bus portion comprises a plurality of first light guide segments and a plurality of second light guide segments, with neighboring ones of said fist component and said plurality of additional components in said high-frequency shielded volume being connected via one of said first light guide places and one of said second light guide pieces.

5. An electrical apparatus as claimed in claim 4 wherein each of said plurality of double-T couplers is connected to an incoming one of said first light guide segments and incoming one of sold second light guide segments, and is connected to an outgoing one of said first light guide segments and to an outgoing one of said second light guide segments, and wherein each of said double-T couplers comprises a first optical receiver coupled to said incoming one of said first light guide segments, a second optical receiver coupled to said incoming one of said second light guide segments, a first optical transmitter coupled to said outgoing one of said first light guide segments, and a second optical transmitter coupled to said second outgoing one of said second light guide segments.

6. An electrical apparatus as claimed in claim 5 wherein said plurality of double-T couplers are disposed in a sequence in said high-frequency shielded volume, said sequence including a first of said double-T couplers, and wherein said electro-optical interface contains an optical transmitter coupled to the first incoming one of said first light guide segments of said first of said double-T couplers, and an optical receiver coupled to the first outgoing one of said second light guide segments of said first of said double-T couplers.

7. An electrical apparatus as claimed in claim 1 wherein said first bus portion comprises a twisted pair wire bus.

8. An electrical apparatus as claimed in claim 1 wherein said sensor/actuator bus comprises a multi-master bus.

9. An electrical apparatus as claimed in claim 8 wherein said sensor/actuator bus comprises a Controller Area Network bus.

10. An electrical apparatus as claimed in claim 9 wherein said second bus portion comprises an optical system having a dominant bit level designated by "light on" and a recessive bit level designated by "light off".

11. An electrical apparatus as claimed in claim 1 wherein said high-frequency shielded volume comprises a high-frequency shielded room containing a magnetic resonance data-obtaining system of a diagnostic magnetic resonance apparatus having a plurality of components, and wherein said first component comprises a component of said system.

* * * * *